United States Patent
Scholl et al.

(10) Patent No.: US 8,688,185 B2
(45) Date of Patent: Apr. 1, 2014

(54) DEVICE FOR MEASURING BLOOD, TISSUE, AND SKIN PARAMETERS

(75) Inventors: Thomas Scholl, Wismar (DE); Martin Eckermann, Rostock (DE); Marko Sproessel, Wismar (DE)

(73) Assignee: EnviteC-Wismar GmbH, Wismar (DE)

( * ) Notice: Subject to any disclaimer, the term of this patent is extended or adjusted under 35 U.S.C. 154(b) by 654 days.

(21) Appl. No.: 12/641,677

(22) Filed: Dec. 18, 2009

(65) Prior Publication Data

US 2011/0152649 A1 Jun. 23, 2011

(51) Int. Cl.
*A61B 5/00* (2006.01)
(52) U.S. Cl.
USPC .......................................................... 600/323
(58) Field of Classification Search
USPC ........................................................ 600/323
See application file for complete search history.

(56) References Cited

U.S. PATENT DOCUMENTS

| | | | |
|---|---|---|---|
| 2006/0149149 A1* | 7/2006 | Schmid | 600/473 |
| 2007/0219440 A1* | 9/2007 | Hannula et al. | 600/323 |
| 2008/0076987 A1* | 3/2008 | Arizaga Ballesteros | 600/323 |
| 2008/0132769 A1* | 6/2008 | Henderson et al. | 600/301 |
| 2009/0076405 A1* | 3/2009 | Amurthur et al. | 600/529 |
| 2010/0168539 A1* | 7/2010 | Palerm et al. | 600/365 |

* cited by examiner

*Primary Examiner* — Clayton E Laballe
*Assistant Examiner* — Dennis Hancock
(74) *Attorney, Agent, or Firm* — Chalin A. Smith; Smith Patent Consulting

(57) ABSTRACT

The invention relates to a device and a method for measuring blood, tissue, or skin parameters, in particular the oxygen saturation in blood, by attaching one or more sensors to body parts such as fingers, earlobes, toes, hand, or foot. The invention relates further to a method for the preparation of said device.

16 Claims, 1 Drawing Sheet

DEVICE FOR MEASURING BLOOD, TISSUE, AND SKIN PARAMETERS

FIELD OF THE INVENTION

The invention relates to a device and a method for measuring blood, tissue, or skin parameters, in particular the oxygen saturation in blood, by attaching one or more sensors to body parts such as fingers, earlobes, toes, hands, and feet. The invention further relates to a method for the preparation of said device.

BACKGROUND TO THE INVENTION

The pulse oximetry via SpO2 sensor technology with non-invasive technique for the continuous measurement of arterial oxygen saturation of the blood has already been well established in the field of patient monitoring. Here, a distinction is made between disposable SpO2 sensors for single use and reusable SpO2 sensors for repeated use.

A disposable SpO2 sensor is in particular used for the continuous observation or long-term monitoring of patients that have to be monitored over several hours, more particularly over several days to ensure maintenance of a healthy state. In use, the disposable SpO2 sensor is applied onto predetermined positions at the body and fixed. After a certain utilization period, as a rule after eight hours, this sensor has to be newly applied to another place of the body. The background to this is to ensure that the sensor does not cause and exercise any negative effects such as undue pressure, temperature, or allergic reactions on this place of body. In addition, in case of reapplication, there is also ensured that the medical skilled person will check that the sensor is functioning properly. An essential advantage of disposable sensors over reusable sensors is given by their construction and fixation to the human body.

The disposable sensor is characterized by its low mass and by the plaster tape material, which at the same time also presents a cost-effective technical variation. Hereby, motion artifacts and hence measuring errors in the patient monitoring at the SpO2 monitor are reduced or excluded, respectively. These are the essential requirements that are necessary for the employment of sensors with newborns and neonates. As many neonates have to be monitored after their birth over several hours, e.g., up to 72 hours, to ensure proper lung function, the employment of an SpO2 disposable sensor is absolutely imperative.

A typical application of the disposable SpO2 sensor involves attachment to the hand or foot of a baby. Since the baby is moving all the time during the period of monitoring, a safe and strong application of the sensor is necessary. The sensor must not slip off from the site of application, from the foot or from the hand, by itself.

Furthermore, it has to be ensured that the SpO2 sensor does not pose a threat to the patient. For example, there could be caused burns at the baby's skin as well as pressure sores of the sensor by a too tight application or allergic reactions by the adhesive material of the plaster tapes at the skin surface.

Therefore, an international norm does exist, the ISO 9919, for all SpO2 monitors and the corresponding SpO2 sensors. Herein, the exact demands on each sensor, and monitor manufacturer are defined also with respect to the sensor's safety requirements.

From the company DIXTAL Medical Inc. (U.S. Pat. No. 6,073,038; U.S. Pat. No. 6,149,481; U.S. Pat. No. 5,891,026), the construction and employment of a neonate pediatric SpO2 sensor is known. Such sensors are characterized by a foam wrap base material, onto which are fixed, by two additional adhesive tapes, a cable and the SpO2 optics soldered thereto composing of SpO2 LEDs and a detector. Generally, the optics and the cable are fixed between two very thin adhesive tapes, which are arranged on the upper side of the fixing strap. Essential disadvantages of such a sensor are:

insufficient fixation of the optics and the cable between the two thin adhesive tapes, wherein there is a risk that mechanical stress, such as pulling the cable when the sensor is applied, may result in the cable together with the optics being pulled out of the disposable sensor;

lack of strain relief by the cable at the sensor, such that moving the cable may result in its release from between the two adhesive tapes;

insufficient protection of the optics and the electric contacts such as cable and stranded wires against penetration of liquids in accordance with the requirements by the norm;

insufficient resistance to movement, wherein the sensor can not be sufficiently fixed at the body, since the thin adhesive tape that holds the optics has insufficient skid resisting properties;

insufficient padding of the sensor against pressure sores at the positions where the optics are located, with the optics separated from the baby's skin by only a very slim tape;

insufficient protection of said sensor from contact discharge, wherein high voltage is not given at a prescribed dielectric strength of 4 kV, since the insulation takes place by only a thin film.

SUMMARY OF THE INVENTION

An object of the invention was to provide a device for measuring blood, tissue, or skin parameters, in particular the oxygen saturation in blood, which does not exhibit the mentioned disadvantages and further: (i) includes a moisture-tight cover that safely encloses the transmitting and receiving units using only a few single elements, (ii) guarantees a high operational reliability under changing stresses, and (iii) attaches easily to body parts of differing sizes. In addition, through the inclusion of the few single elements, the device may be rapidly and easily and hence cost-effectively prepared.

According to the invention this object is solved by the device according to claim 1. In particular, the device of the present invention comprises a flexible fixing strap comprised of an upper part having a fastening member of a hook-and-loop material such as VELCRO® arranged at one end thereof, and a plastic foam-like, in particular skid-resistant, lower part, the device being characterized in that between upper part and lower part a transmitting optics and a detector are arranged, and moisture-tight encapsulated, with a connecting cable disposed between the two halves of a foldable capsule band provided with self-adherent inner surfaces.

As the transmitting optics there are used one or more, preferably two common LEDs known to the skilled person which emit light and introduce it to the patient. The detector is used as an optical receiver for the light from the patient.

Preferably, the connecting cable is fastened to the fixing strap by a strain relief band. In this example, the connecting cable is wrapped with the strain relief band, the strain relief band being connected in a tension-proof manner with the transmitting optics and detector via the fixing strap. In one embodiment, the strain relief band is a self-adherent film that wraps a part of the fixing strap as well as the connecting cable.

In a further embodiment, the upper part of the device according to the invention is formed of a tension-proof material and connected with the plastic foam-like lower part by a hook-and-loop fastening material such as VELCRO®. Alternatively, the upper part may be connected with the plastic foam-like lower part in a self-adherent way.

The device in accordance to the invention preferably has windows in the area of transmitting optics and detector both in the capsule band and in the lower part of the fixing strap, so that the light emitted from the transmitting optics can reach the bodily organ of the patient and from there can come back to the detector. The windows are either just openings or areas that are composed of an optically translucent material.

The exterior surface of the upper part of the fixing strap is preferably formed of a hook-and-loop material such as VELCRO® that may be connected the hook-and-loop fastening member arranged at one end of the fixing strap. In this way, the device can be attached in a flexible and essentially pressure-free manner to the desired bodily organ.

In a further embodiment the foldable capsule band of the device according to the invention is composed of a mainly white, moisture-impermeable material, for example a white plastic film.

The present invention relates further to a method for measuring blood, tissue, or skin parameters, in particular the oxygen saturation in blood, characterized in that a device as described above is attached to a body part, such as a finger, toe, earlobe, hand, or foot. Then the connecting cable can be connected with a corresponding evaluation unit which for example determines and displays the oxygen saturation in the patient's blood via the light received by the detector.

Though the inclusion of only few single elements as compared to other known sensors, it is possible to prepare a device according to the invention in an easy and fast and hence cost-effective way. For example, a sensor unit composed of the LED or LEDs, the detector, and the connecting cable is first positioned on one of the halves of a foldable capsule band having a self-adhering inner surface. Subsequently, a mainly self-adhering strain relief band is fixed to the connecting cable to provide the strain relief to the sensor unit in case of mechanical stresses. By folding over the second half of the foldable capsule band onto the first half, the now complete sensor unit is adhesively closed in a moisture-tight seal.

This covered-over sensor unit may now be positioned and fixed to the inner surface of the upper part of the fixing strap. After this, the plastic foam-like lower part of the fixing strap that is congruent with the upper part of the fixing strap is adhesively connected to the upper part and sensor unit. As a final step, the strain relief band is fully wrapped around the connecting cable to afford the strain relief.

The invention is now discussed in detail regarding the example without considering it as limiting.

DETAILED DESCRIPTION OF THE INVENTION

Figure 1:
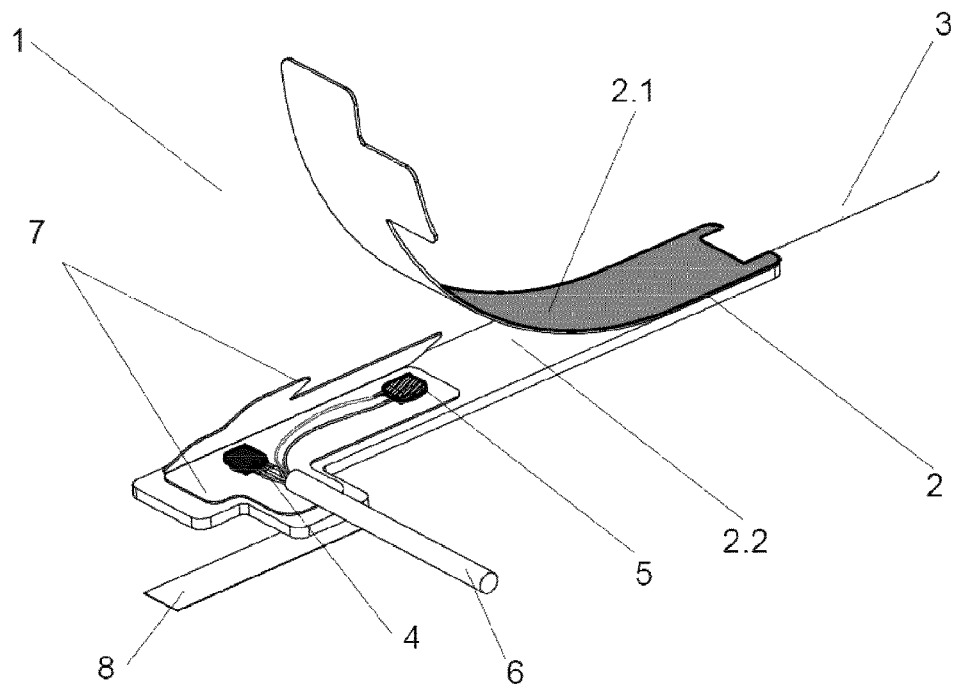
FIG. 1 shows an opened up view of a sensor in accordance with the present invention.

FIG. 1 shows an opened-up view of an example sensor of the present invention. The sensor (1) includes a fixing strap (2) formed from the adherence of a tension-proof upper part (2.1) to a congruent plastic foam-like lower part (2.2).

With reference to FIG. 1, the upper part (2.1) has an exterior (upper) surface of a hook-and-loop material such as VELCRO® and an interior (lower) surface of a self-adherent material. The upper part (2.1) further includes a hook-and-loop fastening member (3) that permits a variable length adjustment when the sensor (1) is attached to a body part such as foot, toe, or hand.

In assembly, transmitting optics (4) and detector (5) are positioned adhesively on one half of a foldable capsule band (7) provided with strain relief band (8). Once in place, the other half of the capsule band (7) is folded and pressed onto transmitting optics (4) and detector (5) to provide a moisture-tight covering. The strain relief band (8), designed to be self-adherent on one side, is then wrapped around the connecting cable (6) to secure the position of transmitting optics (4) and detector (5) at the connecting cable (6) in case of mechanical stresses. The capsule band (7), which in this example is white, is preferably designed to be adhesive on both sides so that it may both cover over transmitting optics (4) and detector (5) in a self-adherent, moisture-tight manner and be self-adherently arranged between upper part (2.1) and lower part (2.2). In this way, the capsule band (7) provides additional strain relief for the transmitting optics (4) and detector (5).

Figure 2:
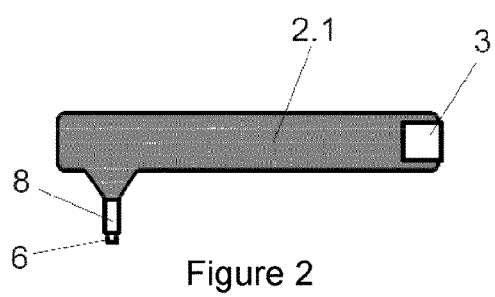
FIG. 2 shows the top view of the sensor of FIG. 1.

FIG. 2 shows a top-down view of the sensor of FIG. 1. The tension-proof upper part (2.1) of the sensor (1) a has a fastening member (3) of a hook-and-loop material such as VELCRO® arranged at the end. The upper part (2.1) of the sensor (1) further includes an exterior (upper) surface of a hook-and-loop material such as VELCRO® to which a corresponding hook-and-loop fastening member (3) can be connected in a length-variable form-closed fashion.

The self-adherent strain relief band (8) is wrapped about the connecting cable (6) to provide strain relief and thereby ensure the required high operational reliability of the measuring method in case of mechanical stresses of the connecting cable (6) by tensile stresses.

Figure 3:
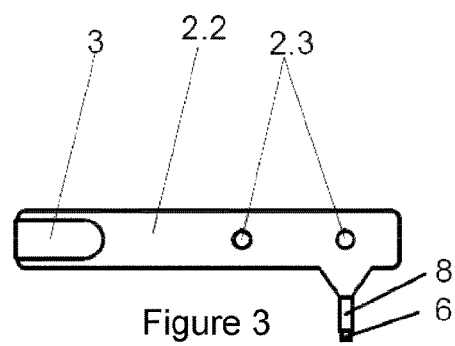
FIG. 3 shows the bottom view of the sensor of FIG. 1.

FIG. 3 presents a bottom-up view of the assembled sensor (1) with its plastic foam-like lower part (2.2) that can be padded as well as the windows (2.3) for light of the transmitting and receiving optics. Further there can be seen the folded hook-and-loop fastening member (3) as well as the connecting cable (6) with the strain relief band (8) wrapped around the connecting cable (6) for the relief of strain resulting from mechanical stresses.

The invention claimed is:

1. A device for measuring blood, tissue, or skin parameters, including oxygen saturation in blood, through attachment to bodily organs, said device comprising:
   a flexible fixing strap (2) having a length defined by a longitudinal axis, wherein said flexible fixing strap is comprised of a tension-proof upper part (2.1) having a hook-and-loop fastening member (3) arranged thereto at one end and a plastic foam-like, skid-resistant lower part (2.2) congruent in size and shape with said upper part;
   a foldable capsule band (7) comprised of mating first and second halves and a self-adherent inner surface, wherein neither said first half nor said second half is congruent in size with either the upper part or the lower part of said flexible fixing strap;
   a transmitting optics (4), a detector (5), and a connecting cable (6) mounted to the first half of said capsule band by means of said self-adherent inner surface and then covered by the second half of said capsule band to yield a sealed, moisture-tight sensor unit, wherein said sensor unit has a length defined by a longitudinal axis whereby the length of said sensor unit is less than the length of said flexible fixing strap, further wherein said sensor unit is arranged between said upper and lower parts of said fixing strap; and
   a strain relief band;

wrapped around said connecting cable so as to further secure said sensor unit to said fixing strap.

2. The device according to claim 1, characterized in that the strain relief band is self-adhering.

3. The device according to claim 1, characterized in that a lower surface of said upper part (2.1) is connected to an upper surface of said lower part (2.2) by a layer of hook-and-loop material.

4. The device according to claim 1, characterized in that a lower surface of said upper part (2.1) is connected to an upper surface of said lower part (2.2) by a layer of adhesive.

5. The device according to claim 1, characterized in that the capsule band (7) and the lower part (2.2) are provided with windows (2.3) in the area of the transmitting optics (4) and the detector (5).

6. The device according to claim 1, characterized in that the upper part (2.1) has an upper surface formed of a hook-and-loop material.

7. The device according to claim 1, characterized in that the connecting cable (6) is disposed between the upper and lower parts of said fixing strap and thus the strain relief band (8) is wrapped around both the connecting cable (6) and the upper part (2.1) and the lower part (2.2) of the fixing strap (2).

8. The device according to claim 1, characterized in that the foldable capsule band (7) is composed of a mainly white moisture-impermeable material.

9. A method for measuring blood, tissue, or skin parameters, including oxygen saturation in blood, characterized in that a device according to claim 1 is attached to a body part selected from among fingers, toes, earlobes, hands, and feet.

10. A method for the preparation of a device for measuring blood, tissue, or skin parameters, including oxygen saturation in blood, through attachment to bodily organs, said method comprising the steps of:
  a. providing a flexible fixing strap (2) having a length defined by a longitudinal axis, wherein said flexible fixing strap is comprised of a tension-proof upper part (2.1) having a hook-and-loop fastening member (3) arranged thereto at one end and a plastic foam-like, skid-resistant lower part (2.2) congruent in size and shape with said upper part;
  b. providing a foldable capsule band (7) comprised of mating first and second halves and a self-adherent inner surface, wherein neither said first half nor said second half is congruent in size with either the upper part or the lower part of said flexible fixing strap;
  c. adhesively mounting a transmitting optics (4), a detector (5) and a connecting cable (6) to the first half of said capsule band;
  d. folding the second half of said capsule band over the first half of said capsule band, thereby covering said transmitting optics (4), a detector (5) and a connecting cable (6) to yield a sealed, moisture tight sensor unit, wherein said sensor unit has a length defined by a longitudinal axis whereby the length of said sensor unit is less than the length of said flexible fixing strap;
  e. arranging said sealed sensor unit between said upper and lower parts of said fixing strap; and
  f. wrapping a strain relief band around said connecting cable so as to further secure said sensor unit to said fixing strap.

11. The method according to claim 10, wherein a lower surface of the upper part (2.1) is connected to an upper surface of the lower part (2.2) by a layer of hook-and-loop material.

12. The method according to claim 10, wherein a lower surface of the upper part (2.1) is connected to an upper surface of the lower part (2.2) by a layer of adhesive.

13. The method according to claim 10, wherein the capsule band (7) and the lower part (2.2) are provided with windows (2.3) in the area of the transmitting optics (4) and the detector (5).

14. The method according to claim 10, wherein the upper part (2.1) has an upper surface formed of a hook-and-loop material.

15. The method according to claim 10, wherein the connecting cable (6) is disposed between the upper and lower parts of said fixing strap and thus the strain relief band (8) wraps around the upper and lower parts of said fixing strap (2) in addition to said connecting cable (6).

16. The method according to claim 10, wherein the foldable capsule band (7) is composed of a mainly white moisture-impermeable material.

* * * * *